(12) United States Patent
O'Brien

(10) Patent No.: US 7,064,188 B2
(45) Date of Patent: Jun. 20, 2006

(54) MONOCLONAL ANTIBODIES WHICH IDENTIFY THE GLYCOPROTEIN CARRYING THE CA125 EPITOPE

(75) Inventor: Timothy J. O'Brien, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 301 days.

(21) Appl. No.: 10/237,920

(22) Filed: Sep. 9, 2002

(65) Prior Publication Data

US 2003/0082655 A1 May 1, 2003

Related U.S. Application Data

(63) Continuation of application No. 09/069,471, filed on Apr. 29, 1998, now abandoned, which is a continuation of application No. 08/626,675, filed on Apr. 2, 1996, now Pat. No. 5,976,818, which is a continuation of application No. 08/343,357, filed on Nov. 22, 1994, now abandoned, which is a continuation of application No. 07/808,219, filed on Dec. 16, 1991, now abandoned.

(51) Int. Cl.
*C07K 16/00* (2006.01)

(52) U.S. Cl. .............. 530/388.8; 530/387.1; 530/387.7; 530/388.1; 530/388.85; 530/389.1; 530/389.7; 435/326; 435/330; 435/344.1

(58) Field of Classification Search ........ 435/326, 435/330, 344.1; 530/387.1, 387.7, 388.1, 530/388.8, 388.85, 389.1, 389.7
See application file for complete search history.

(56) References Cited

U.S. PATENT DOCUMENTS 4,921,790 A * 5/1990 O'Brien .................. 435/7.94

5,650,291 A 7/1997 Lee

OTHER PUBLICATIONS

Sakahara et al Gynecologic Oncology vol. 52 p. 301 (1994).*

Kabawat et al., *Tissue Distribution of a Coelomic-Epithelium-Related Antigen Recognized by the Monoclonal Antibody OC125*, International Journal of Gynecological Pathology, 1983, vol. 2, pp. 275-285.

O'Brien et al., *CA 125 antigen in human amniotic fluid and fetal membranes*, Am. J. Obstet Gynecol, 1986, vol. 155, pp. 50-55.

Hudson and Hay, Practical Immunology, Blackwell Scientific Publications, 1976, Oxford, p. 10.

de St. Groth et al., *Production of Monoclonal Antibodies: Strategy and Tactics*, J. Immunol Meth, 1980, vol. 35, pp. 1-21.

Davis et al, *Characterization of the CA 125 Antigen Associated with Human Epithelial Ovarian Carcinomas*, 1986, vol. 46, pp. 6143-6148.

Hardardottier et al. "Distribution of CA 125 in embryonic tissues and adult derivatives of the fetal periderm" Am. J. Obstet. and Gynecol. vol. 165. No. 6. part 1. pp. 1925-1931.

Jacobs et al. "The CA 125 tumour-associated antigen: a review of the literature" Human Reproduction. vol. 4 No. 1 p. 1-12.

* cited by examiner

*Primary Examiner*—Sheela J. Huff
(74) *Attorney, Agent, or Firm*—Bell, Boyd & Lloyd LLC

(57) ABSTRACT

Hybridomally produced monoclonal antibodies specifically immunoreactive with the glycoprotein carrying the CA 125 epitope. Monoclonal antibodies recognize both high and low molecular weight subunits of the antigen, and identify the antigen in the cytoplasm and the extracellular matrix of CA 125 producing cells. An immunoassay for the detection of CA 125 utilizing the monoclonal antibodies is described.

7 Claims, 3 Drawing Sheets

MONOCLONAL ANTIBODIES WHICH IDENTIFY THE GLYCOPROTEIN CARRYING THE CA125 EPITOPE

The present application is a continuation of application Ser. No. 09/069,471, filed Apr. 29, 1998, now abandoned, which is a continuation of application Ser. No. 08/626,675, filed Apr. 2, 1996, now U.S. Pat. No. 5,976,818, issued on Nov. 2, 1999, which is a continuation of application Ser. No. 08/343,357, filed Nov. 22, 1994, now abandoned, which is a continuation of application Ser. No. 07/808,219, filed Dec. 16, 1991, now abandoned.

BACKGROUND OF THE INVENTION

The invention described herein was supported by National Institute of Health Grant #ROICA40406.

The present invention relates to the identification and use of monoclonal antibodies specific for the glycoprotein antigen complex carrying the CA 125 epitope.

CA 125 is an antigenic determinant or epitope located on the surface of ovarian tumor cells with essentially no expression in normal adult ovarian tissue. However, CA 125 is expressed on the cell surface of tumor cells in culture and on ovarian tumor lesions. Significantly, CA 125 is elevated in the sera of patients (>90%) with ovarian adenocarcinoma. In fact, CA 125 is regularly detected on the tumor cell surface and in the serum of patients with serous cystadenocarcinoma of the ovary (>95%). Expression of this antigen occurs less frequently in endometrial and clear cell carcinomas, and essentially no expression is detected in mucinous cystadenocarcinomas. Although not exclusively found in the blood of these patients, CA 125 has been detected in the sera of a significant percentage of patients with pancreatic carcinoma (approximately 50%) and with liver and colon carcinoma (approximately 22–32%).

The presence of CA 125 in high concentrations in the serum of patients with ovarian adenocarcinoma has been widely used by health care providers in the treatment and management of such patients. Although CA 125 is not specific for ovarian carcinoma, there is, nonetheless, a direct correlation between the presence of CA 125 and disease status i.e., progression, regression, or no change. Since almost all ovarian cancer patients receive extensive chemotherapy, CA 125 is used as an indicator of a disease free state. Further, increased serum concentrations of CA 125 precede clinical diagnosis of recurrent disease by a period of approximately one to four months. As a result, assay of this tumor marker is becoming a standard diagnostic tool in monitoring ovarian cancer patients.

As previously described, CA 125 is not an exclusive product of ovarian cancer cells. Like many other tumor markers, CA 125 is also expressed normally in early fetal development. For example, Kabawat et al. (Int J Gynecol Pathol, 2:275–85 (1983)) demonstrates the presence of traces of CA 125 in fetal tissues; the antigen was localized to the amnion and derivatives of muellerian epithelium, and coelomic epithelium (including the peritoneum, pleura and pericardium). In adult tissues, Kabawat et al. and Hardardottir et al. (Am J Obstet Gynecol, 163:1925–1931 (1990)) report that the monoclonal antibody, OC 125, reacts with the epithelium of the fallopian tube, endometrium, and endocervix, and is also expressed in the apocrine sweat glands and the mammary glands. Hardardottir et al. further discloses the presence of CA 125 antigen during fetal development in notochord, myocardium, pericardium, the mesonephric duct, the vitelline and allantoic ducts, as well as the amnion and periderm. Elevations of serum CA 125 in patients with endometriosis, during menses, and in early gestation further demonstrates expression of this antigen during normal growth and development. The abundance of the antigen in breast milk, benign ovarian cyst fluid, and amniotic fluid further implicate CA 125 in normal cell growth and development.

Little is known of the structure of the CA 125 antigen or the metabolic regulation or expression of this antigen in either normal or neoplastic tissues. Current state of the art discloses that CA 125 is part of a large molecular weight mucin-like glycoprotein complex, which can be resolved to a 200 kd–250 kd species on SDS acrylamide or agarose-acrylamide gels. Based on the presence of sugar residues, buoyant density studies, and lectin binding properties, the CA 125 antigen is thought to contain a carbohydrate component. However, the antigenic epitope that is recognized by the monoclonal antibody, OC 125, is considered to be peptidic in nature, because of its sensitivity to proteases like trypsin and V8 protease and its relative stability to glycosidases.

It would be highly desirable to gain a better understanding of the structure and function of the CA 125 antigen, especially through the development of new reagents to map protein domains. The development of new reagents such as monoclonal antibodies would likely provide a basis for new immunoassays with improved sensitivity and specificity for the detection of CA 125 antigen.

SUMMARY OF THE INVENTION

The present invention provides hybridomally produced monoclonal antibodies that are specifically immunoreactive with the glycoprotein carrying the CA 125 epitope. The monoclonal antibodies have a binding affinity for a high molecular weight (~>200 kd) subunit and a lower molecular weight subunit (68 kd) of the CA 125 antigen. These antibodies recognize the antigen in the cytoplasm and the extracellular matrix of CA 125 producing cells. The present invention contemplates the use of the monoclonal antibodies in improving the assay and immunohistologic detection of the CA 125 antigen. Since the antibodies recognize the cell surface component of tumor cells, it is further anticipated that the antibodies would provide a means of delivering imaging isotopes and chemotherapeutic agents to tumor cells, thereby enhancing the diagnosis and treatment of neoplasms.

In one embodiment of the present invention, a monoclonal antibody specifically immunoreactive with the glycoprotein carrying the CA 125 epitope is identified as having a binding affinity for a subunit of the CA 125 epitope having a molecular weight of greater than approximately 200 k daltons.

In another embodiment, a monoclonal antibody specifically immunoreactive with the glycoprotein carrying the CA 125 epitope is identified as having a binding affinity for a subunit of the CA 125 epitope having a molecular weight of approximately 68 k daltons.

In a further embodiment, a monoclonal antibody specifically immunoreactive with the glycoprotein carrying the CA 125 epitope and identified as M2 is located predominantly in the cytoplasm of CA 125 producing cells.

In yet another embodiment, a monoclonal antibody specifically immunoreactive with the glycoprotein carrying the CA 125 epitope and identified as M11 is located predominantly in the extracellular matrix of CA 125 producing cells.

Additional features and advantages of the present invention are further described, and will be apparent from the presently preferred embodiments.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

Hybridomas producing MAb identified as M11 (PTA-6206) has been deposited with the American Type Culture Collection, 10801 University Boulevard, Manassas, Va. 20110-2209 under the Budapest Treaty and given the Accession No. PTA-6206 on Sep. 14, 2004.

Figure 2:
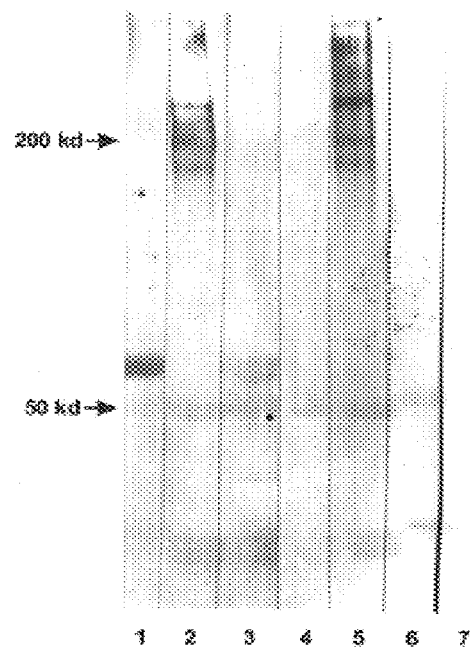

FIG. 2 illustrates immunoprecipitation of ascites fluid CA 125 antigen using newly developed monoclonal antibodies followed by western blotting and probing of individual lanes with homologous monoclonal antibody. Lanes 1–7 were individually probed with M1, M2, M3, M6, M11, M12 and control mouse ascites, respectively.

Figure 3:
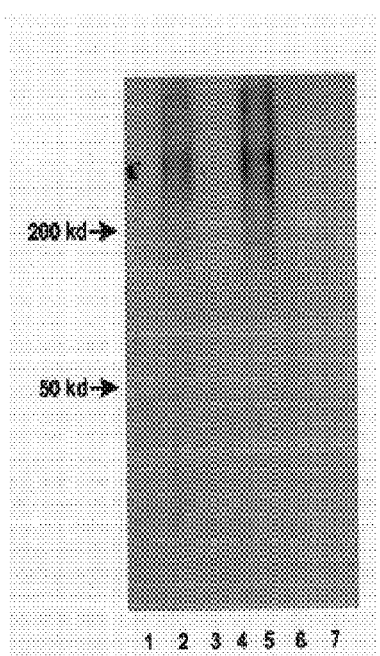

FIG. 3 illustrates immunoprecipitation of ascites fluid CA 125 followed by western blotting of precipitates as described in FIG. 2, but individual lanes were probed with $^{125}$I-OC 125.

Figure 4:
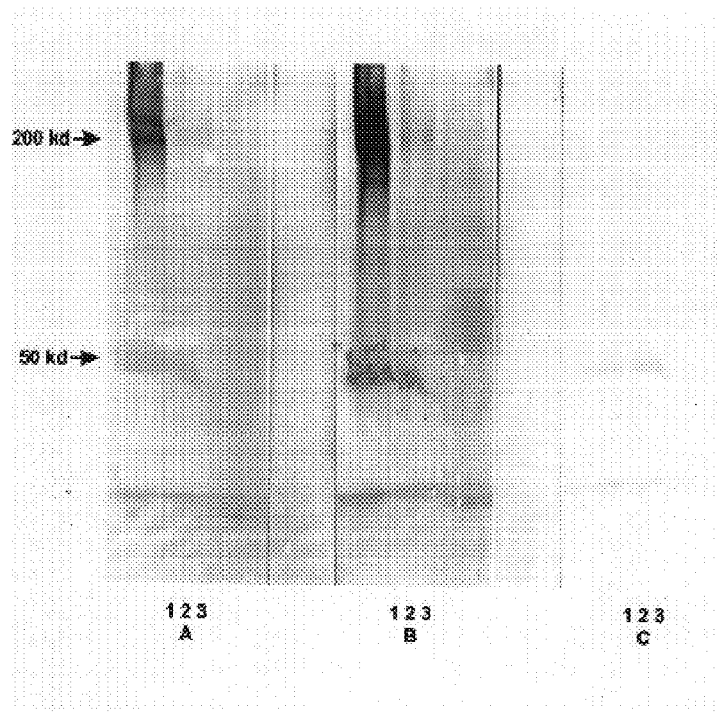

FIG. 4 illustrates immunoprecipitation of CA 125 from ascites fluid, amniotic fluid, and normal human serum (Lanes 1–3) with monoclonal antibody M2 (Panel A), M11 (Panel B), and control ascites (Panel C) followed by western blotting and probing with homologous antibodies.

Figure 5:
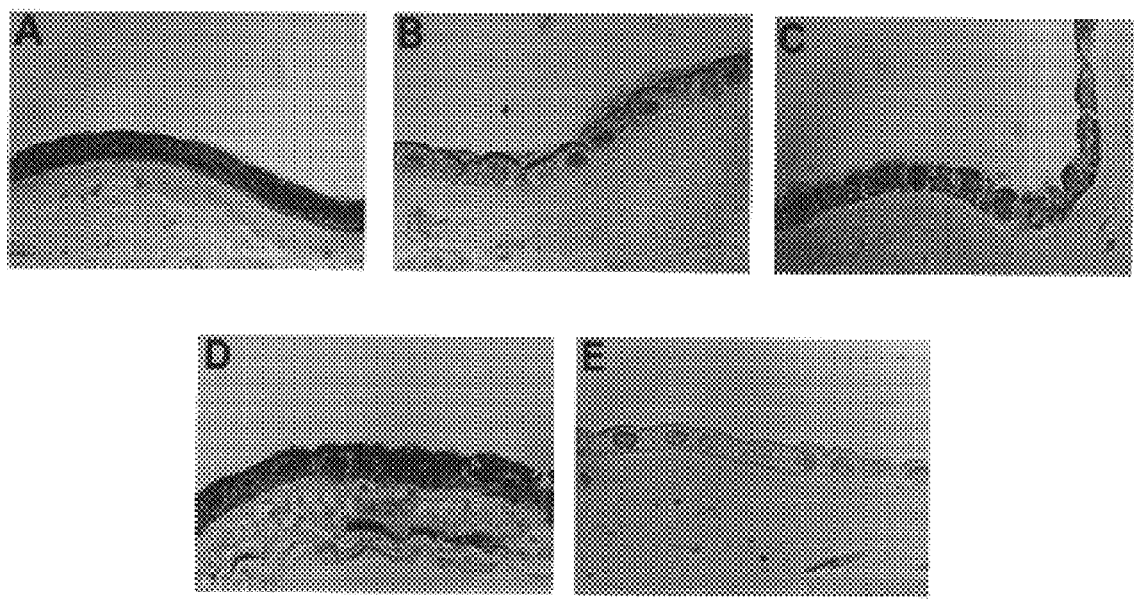

FIG. 5 illustrates immunolocalization of CA 125 antigen in amnion epithelium (magnification×100) using M2 (Panel A), M11 (Panel B), M1 (Panel C), OC 125 (Panel D), and control mouse ascites (Panel E).

DETAILED DESCRIPTION OF THE PRESENTLY PREFERRED EMBODIMENTS

The present invention provides new monoclonal antibodies that are specific for the glycoprotein antigen complex carrying CA 125, an epitope located on the surface of ovarian carcinoma cells. More specifically, the present invention provides hybridomas that are capable of producing monoclonal antibodies which exhibit a greater binding affinity for the CA 125 antigen than has been previously heretofore observed.

Use of the hybridomally produced monoclonal antibodies of the present invention results in improved assay and immunohistologic detection of the CA 125 antigen, thereby providing the basis for the development of new, diagnostic immunoassays for the detection and monitoring of serum CA 125.

As will be shown in the following detailed embodiments, the immunizing antigen, CA 125, was derived from ascites fluid and partially purified by the method described by O'Brien et al., Am J Obstet Gynecol, 155:50–55 (1986). Balb/c mice were administered dosages of the CA 125 antigen intraperitoneally at three different times. Following the third dosage, the spleens were harvested for fusion with mouse myeloma cells, thereby forming hybridomas. The resulting hybridomas were analyzed for antibody activity and found to secrete antibodies specific against the CA 125 antigen.

Competition studies were then conducted utilizing the 12 positive hybridomas which recognized CA 125 rich test material. These hybridomas were incubated with $^{125}$I-OC 125 antibody in a binding assay for the CA 125 antigen. As will be shown in the following example, monoclonal antibody, M2, competed effectively for a site similar to or the same as the OC 125 antibody.

Similar studies were carried out by preloading individual OC 125 beads with CA 125 antigen obtained from normal human serum, tumor serum, ascites fluid, breast milk, and amniotic fluid containing high levels of CA 125. CA 125 beads were then exposed individually to monoclonal antibodies, M2 or M11, or to a control in the presence of $^{125}$I-OC 125. These studies revealed that M2 antibody competed effectively with $^{125}$I-OC 125 antibody regardless of the source of the CA 125 antigen. Additional immunohistochemical studies further demonstrated recognition of the CA 125 antigen by monoclonal antibodies, M2 and M11, within cells also recognized by the monoclonal antibody, OC 125.

By way of example, and not limitation, the following examples and drawings serve to further illustrate the present invention in its preferred embodiments.

EXAMPLE I

This example illustrates the formation of hybridomas, the source of monoclonal antibodies specific to the glycoprotein antigen complex carrying the CA 125 epitope, and the resulting monoclonal antibodies.

Preparation of Immunizing Antigen

CA 125 antigen derived from ascites fluid was partially purified (approximately 2000 units/ug protein) using the method described by O'Brien et al., Am J Obstet Gynecol, 155:50–55 (1986). The antigen was precipitated with alum according to the procedure of Hudson and Hay, Practical Immunology, Blackwell Scientific Publications, Oxford, p. 10 (1976). The resulting precipitate was washed twice with 15 ul volume of 0.01 M phosphate buffered saline consisting of 0.15 M NaCl at pH 7.2 (hereinafter "PBS"). The pellet was suspended in 50 ul of PBS and maintained at 4° C. until use.

Immunization of Balb/c Mice

Balb/c mice were immunized by intraperitoneal injection of 20 ug of alum precipitated antigen in 100 ul of PBS containing $10^9$ killed bordetella pertussis organisms (obtained from the Michigan Department of Health Lansing, Mich.). After 4 weeks, mice were challenged again by intraperitoneal injection of a 20 ug of soluble antigen in PBS. Two weeks later, the mice were further challenged with 20 ug of soluble antigen by intraperitoneal injection. Three days later, spleens were harvested for fusion with mouse myeloma cells.

Formation of and Cloning Hybridomas

Fusion of immune mouse splenocytes and 8-azo-guanine resistant P3X63- Ag8.653 mouse myeloma cells was performed according to the procedures described by de St. Groth and Scheidegger, J. Immunol Meth, 35:1–21 (1980). Fifty microliter aliquots of hybridomas were transferred to each well of 5 ninety six well tissue culture plates (Flow Labs), which already contained 200 ul HAT medium ($10^{-4}$ M hypoxanthine, $1.6 \times 10^{-5}$ M thymidine and $4 \times 10^{-7}$ aminopterin) and 3600 mouse peritoneal macrophages. When hybrids developed, the media were screened utilizing a dot blot assay as described in the section below. Positive cultures were cloned utilizing the limiting dilution method in 96 well culture plates. After approximately 2–4 weeks of growth, culture media were again screened and the positive hybrids grown up and recloned.

Screening for CA 125 Antibodies

Culture media were screened using a nitrocellulose dot blot procedure. To this end, ascites fluid with a CA 125 concentration of 22,000 U/ml was diluted 1:20 in PBS. 100 ul were dot blotted to nitrocellulose using a Schleicter and Schuell dot blot apparatus. A control ascites with less than 20 U/ml CA 125 diluted 1:20 was also blotted to nitrocellulose. All blots were rinsed twice with PBS and placed in blotto (5% dry milk powder in PBS) overnight.

Individual dots were cut from the blot and 100 ul of each hybrid culture media were added to tubes containing one control dot (low CA 125) and one test dot (high CA 125). Dots were incubated for 3 hours at room temperature at which time 0.5 ml of blotto was added to each tube and incubated for an additional 10 minutes. All tubes were then aspirated and the dots were washed twice with 1 ml of PBS. Tubes were then incubated with a second antibody, goat-anti-mouse-peroxidase (GAMP, Biorad Corp.), which was diluted 1:250. 250 ul were added to each tube. After the second antibody was incubated for 1 hour at room temperature, the tubes were aspirated. The dots were then washed with PBS and then exposed to horseradish peroxidase color developer (HRP) as described by Biorad Corporation.

Productive cultures were transferred to 1 ml culture dishes and grown up with at least 2 changes of media. Cultures were then screened using a dot blot assay similar to that described hereinabove, except that purified CA 125 was used as the positive test dot. Normal human serum (diluted 1:20) was used as the negative control. Screening was also carried out by saturating OC 125 beads (Centocor Malvern, Pennsylvania) with CA 125 antigen by exposing the beads to 1 ml of ascites fluid containing 22,000 units CA 125/ml overnight at room temperature. The OC 125 beads were then washed twice with 5 ml of PBS and further incubated for 3 hours at room temperature with rabbit antimouse IgG. This was performed in order to saturate any OC 125 antibody not occupied by CA 125 antigen.

After washing, beads were exposed to culture media for 3 hours at room temperature. The beads were washed twice PBS and exposed to peroxidase-coupled antibody (GAMP) and incubated for 1 hour at room temperature. Beads were then aspirated and exposed to peroxidase substrate for color development. Control culture media was used to determine background levels of staining.

Competition Of New Antibodies For OC 125 Epitope

Culture media from positive hybrids along with control culture media (from non-productive wells) were incubated with I-OC 125 antibody in a binding assay for CA 125 antigen. OC 125 beads (Centocor kit) were exposed to 0.4 ml of ascites fluid (22,000 U/ml CA 125) for overnight at room temperature. Beads were washed twice with 5 ml PBS and exposed to 100 ul of $^{125}$I-OC 125 antibody in the presence of 100 ul of culture media from each of he productive hybrids as well as media from two non-productive hybrids for a further 18 hours at room temperature. Beads were washed and counted according to kit instructions. Similar competition studies were carried out by pre-loading individual OC 125 beads with CA 125 antigen obtained from normal human serum, tumor serum, ascites fluid, breast milk, and amniotic fluid which contained high levels of CA 125. CA 125 beads were then exposed individually to hybridomally produced monoclonal antibodies, M2 or M11, or to control culture media in the presence of $^{125}$I-OC 125 as described above.

Groups of 6 Balb/c mice were preconditioned with 0.5 ml peritoneal injections of 0.5 ml of pristane (Aldrich Chemical Co. Milwaukee, Wis.) 14 days prior to injection with $10^6$ hybridoma cells. Ascites fluid was harvested approximately 7–9 days after hybridoma injection. Fluid was centrifuged to remove cells and the supernatent containing monoclonal antibody was stored frozen (−70 degrees) until used.

Immunoprecipitation

Aliquots (500 ul) of normal human serum, amniotic fluid and CA 125 positive ascites fluid were incubated with 100 ul of 1:100 dilution of each of the test monoclonal antibodies and 1 control mouse ascites overnight at 4° C. 200 ul of rabbit antimouse IgG agarose beads (Biorad Corp.) diluted 1:2 were added to each tube and incubated for 4 hours at room temperature with agitation. After centrifugation the beads were aspirated and washed twice with 1 ml buffer (5% albumin in PBS containing 0.1% azide) and twice with 1 ml of Bis-Tris buffer (20 mM Bis Tris propane 7.2). The beads were then exposed to 50 ul of 2× electrophoresis sample buffer for 3 minutes at 100° C. The beads were cooled then pelleted at 2000 RPM for 10 minutes and the supernatant removed for SDS polyacrylamide gel electrophoresis (PAGE).

Electrophoresis/Transblotting

SDS page electrophoresis was carried out on 4–20% gradient polyacrylamide gels according to Laemmli for 4 hours at 30 m amp. After electrophoresis, the gels were soaked in Tris-glycine buffer (24 mM Tris-HCl 192 mM glycine, pH 8.3) and transblotted to an immobilon PVDF filter (Amicon Corp.) using the Tris glycine buffer with 15% (v/v) methanol overnight at 30 volts.

Western Blotting

Immobilon filters were incubated for 30 minutes at room temperature with blotto followed by two washes in PBS for 10 minutes each. Blots are then exposed either to mouse ascites monoclonal antibody at a dilution of 1:100 in PBS or to OC-125-$^{125}$I antibody (Centocor kit) at a 1:10 dilution at 4° C. overnight. The filters were then washed once with blotto for 10 minutes followed by two washes in PBS. The blot was then exposed either to x-ray film overnight if $I^{125}$-OC 125 was used or to peroxidase coupled second antibody, (GAMP) at 1:250 dilution (Biorad Corp.) if mouse monoclonal ascites were used. A second antibody incubation was carried out at room temperature for 1 hour. Filters were washed with blotto and PBS as described above. Blots were developed using HRP color substrate (Biorad Corp.) as described above.

Immuonohistochemistry

For immunohistochemical studies, sections (5 um) of formalin-fixed, paraffin-embedded tissues were deparaffinized and rehydrated through serial alcohol baths to water. The hydrated sections were treated with 3% hydrogen peroxide for 10 minutes to block endogenous peroxidase activity followed by exposure to normal goat serum to reduce non-specific background staining. Primary monoclonal antibody, diluted 1:100 in PBS, was added to sections at room temperature and incubated for 30 minutes. Linking antibody and labelling antibody were applied to tissue sections according to kit instructions supplied by Dako (Santa Barbara, Calif.) 2nd antibody kits. The substrate used for localization of antibody binding was 3-amino-9-ethyl-carbazole (2%). Counter staining was achieved with Mayer's hematoxylin. Negative control slides were prepared in identical fashion using either normal mouse serum or mouse ascites in place of the primary antibody.

Results

The initial screening process of hybrid media utilizing low CA 125 and high CA 125 dot blot analysis yielded 24 wells with a positive dot blot test. A dot was scored positive when staining was present on the test dot (+CA 125) and negative on the control dot (low CA 125). Rescreening of these 24 expanded hybrids utilizing both purified CA 125 and normal human serum (low CA 125) by dot blot analysis and by OC 125 bead binding yielded 12 positive hybrids of CA 125 antibody producing hybridomas as shown in Table I below. Both dot blots and beads were graded visually on a scale of 1 to 4 for color development.

TABLE I

Screening of hybridoma media*

| Culture | Antibody | Dot Blot | Antigen Bead |
|---------|----------|----------|--------------|
| 4A11    | M1       | 3+       | 3+           |
| 3D12    | M2       | 3+       | 3+           |
| 1C2     | M3       | 3+       | 3+           |
| 1B4     | M4       | 2+       | 2+           |
| 2H10    | M5       | 3+       | 2+           |
| 3D6     | M6       | 2+       | 2+           |
| 2E12    | M7       | 2+       | 2+           |
| 1H8     | M8       | 2+       | 2+           |
| 5F12    | M9       | 1+       | 1+           |
| 1C11    | M10      | 1+       | 1+           |
| 2G10    | M11      | 4+       | 2+           |
| 2D12    | M12      | 4+       | 2+           |

*12 of 24 cultures continued to produce antibodies which recognize CA 125 rich test material.

Further analysis of the media from the 12 positive wells by competition analysis utilizing 125I-OC 125 binding to the CA 125 antigen in competition with the individual antibodies present in the positive wells indicated that media from one well described in Table II below as M2 effectively competed for a site similar to or the same as the OC 125 antibody. Control media or other positive media did not compete with $^{125}$I-OC 125 binding to CA 125.

TABLE II

Screening of hybridomas for antibodies which compete with OC 125

| Monoclonal Antibody | % $^{125}$I—OC Bound |
|---------------------|----------------------|
| M1                  | 94                   |
| M2                  | 28                   |
| M3                  | 89                   |
| M4                  | 98                   |
| M5                  | 99                   |
| M6                  | 94                   |
| M7                  | 100                  |
| M8                  | 86                   |
| M9                  | 100                  |
| M10                 | 92                   |
| M11                 | 99                   |
| M12                 | 100                  |
| Control             | 98                   |

After cloning, six hybrids continued to recognize CA 125. These cloned hybridomas were then utilized to produce ascites in pristane treated Balb/e mice. When M2 antibody was produced as ascites, it effectively competed with $^{125}$I-OC 125 regardless of whether the source of CA 125 antigen was serum or ascites obtained from tumor patients or the CA 125 source was obtained from human serum, normal amniotic fluid or breast milk. These results are shown in Table III below.

TABLE III

Competition for CA 125 epitope
% $^{125}$I—OC 125 Bound

|                      | Source of Antigen |                   |                 |                 |                       |
|----------------------|-------------------|-------------------|-----------------|-----------------|-----------------------|
| Competition Medium   | Ascites Fluid     | Amniotic Fluid    | Breast Milk     | Tumor Serum     | Normal Human Serum    |
| Control              | 100               | 100               | 100             | 100             | 100                   |
| M11 Antibody         | 96                | 100               | 98              | 98              | 95                    |
| M2 Antibody          | 0.9               | 1.3               | 2.6             | 1.8             | 2.3                   |

Figure 1:
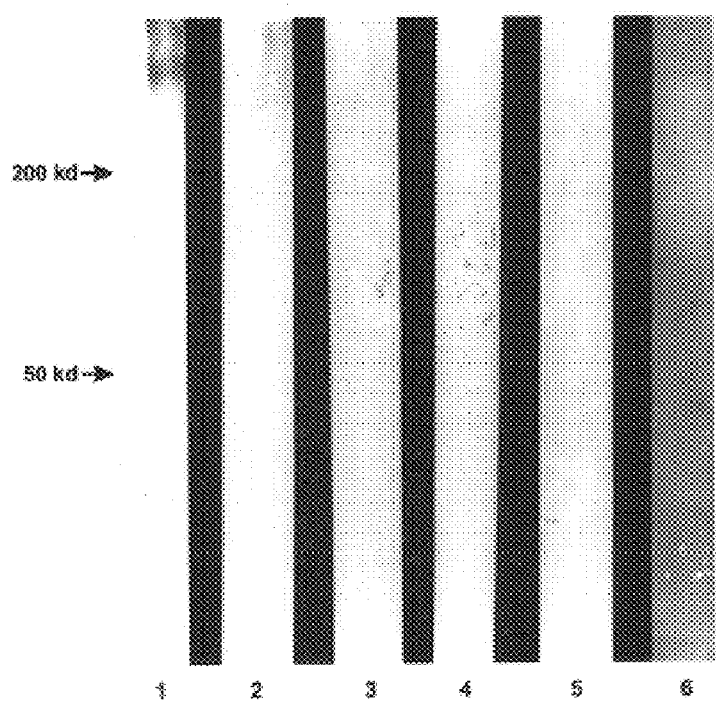
FIG. 1 illustrates a Western blot of CA 125 rich (22,000 U/ml) ascites fluid. Lanes 1–6 were probed with monoclonal antibodies M2, M11, M6, M1, M3 and control mouse ascites, respectively.

Western blot screening of these monoclonal antibodies indicate that antibodies, designated M2 and M11, recognize high molecular antigenic determinants in excess of 200 k daltons as indicated in Lane 1 and Lane 2 of FIG. 1. Electrophoresis patterns of nonpurified CA 125 often give a smudged appearance after blotting. This is due to the association of the antigen with mucin-like high molecular glycoproteins as depicted in Lanes 1 and 2 of FIG. 1. Low intensity binding by M6 in Lane 3 of FIG. 1 is also detectable on the original blot, but is not readily visible in FIG. 1.

Immunoprecipitation of tumor ascites CA 125 antigen was carried out using monoclonal antibodies derived from the six productive hybridomas and the control mouse ascites. This step was followed by electrophoresis, blotting, and probing with homologous antibodies. These results indicate that monoclonal antibodies, M2 and M11, shown in Lanes 2 and 5, respectively, in FIG. 2 recognize multiple high molecular weight antigenic species in excess of 200 k daltons. On the other hand, monoclonal antibody, M1, recognizes a 68 kd subunit, as depicted in Lane 1 of FIG. 2, that is distinct and separate from antibodies M2 and M11.

Immunoprecipitation, electrophoresis, and blotting of a second set of these antibodies probed with the heterologous $^{125}$I-OC 125 antibody indicates that OC 125 recognizes at least one of the molecular species precipitated by both M2 and M11. This is depicted in Lane 2 and Lane 5, respectively, in FIG. 3. No other immunoprecipitate including the 68 kd recognized by M1 was readily detected with OC 125.

Immunoprecipitation of antigen from CA 125 rich sources such as ascites (22,000 u/ml) and amniotic fluid (2,000 u/ml) as well as CA 125 deficient sources such as normal human serum (<10 units CA 125/ml) further demontrate recognition by M2 and M11 of the CA 125 antigen. This is illustrated in FIG. 4, Panels A and B. Immunoprecipitates of ascites from non-immunized mice are shown in Panel C, FIG. 4. Additionally, Lane 1 in each Panel is ascites immunoprecipitate (rich in CA 125), and clearly indicates that M2 (Panel A) recognizes high molecular weight antigen from this source. M2 shows only faint bands for CA 125 antigen derived from the less abundant source of CA 125 amniotic fluid (see Lane 2, Panel B). Essentially no antigen can be detected in immunoprecipitates from normal human serum as shown in Lane 3, Panel B. Similarly, probing with M11 confirms that ascites provides a rich source of CA 125, while amniotic fluid serves as a much poorer source of the antigen. M11 did not bind immunoprecipitates of normal human serum (see Lanes 1–3, Panel B).

On the other hand, the control ascites contained no antibody capable of recognizing CA 125 from all sources of the antigen as illustrated in Panel C of FIG. 4. Bands at 50 kd and approximatley 30 kd represent mouse IgG heavy and light chains recognized by the goat anti-mouse second antibody.

Evaluation of antibodies by immunohistochemical localization in known CA 125 positive tissues further indicates recognition by these antibodies of antigen localized within cells also recognized by the monoclonal antibody OC 125. OC 125 has previously been shown to distinctly stain the single epithelial cellular layer of the amniotic membrane. As illustrated in FIG. 5, comparative staining of monoclonal antibodies M2 (Panel A), M11 (Panel B), M1 (Panel C), and OC 125 (Panel D) along with a mouse ascites control (Panel E) demonstrate the specific localization of these antibodies to the amnion. Distribution of antibody within the amniotic epithelial cells is more evident with M2 (Panel A) and M1 (Panel C), while extracellular or glycocalyx localization of the antibodies is evident with M11 (Panel B) and OC 125 (Panel D).

Expression of CA 125 during fetal development on the epithelium of mullerian duct derivatives (viz the cervix, the corpus and fallopian tube) and on derivatives of coelomic epithelium (peritoneum, pleura and the pericardium) has been documented by Kabawat et al. Expression of the antigen on the developmental sites is maintained throughout adulthood, resulting in the presence of CA 125 in all non-tumor bearing adults. More recently, the inventor and other investigators described the presence of abundant levels of CA 125 in amniotic fluid, and it is now clear that both the amnion and the fetal periderm are major sources of CA 125 during gestation. It is, therefore, somewhat surprising that CA 125 is a useful marker for ovarian cancer in view of the presence of the antigen in abundance in normal tissues. Antigen produced by normal tissues may account for the low but detectable levels of CA 125 which are measurable in both men and women. The large quantities of CA 125 present in the endometrium and cervix are normally secreted to the outside without access to the circulation. In special cases, for example in patients with endometriosis, during menses, and during embryo implantation and early gestation, CA 125 gains access to the circulation through disruption of the endothelium and results in elevated CA 125 levels. In patients with ovarian carcinoma, access to the circulation in measurable amounts occurs relatively late in the disease process. Therefore, most patients with ovarian carcinoma are diagnosed in the advanced stages (e.g. III and IV) when elevated levels of CA 125 might be expected. In fact, at a second look laparotomy when foci of disease are less than 2 cm in size, CA 125 is frequently not elevated or detected in the blood.

It is apparent from the studies described herein that the newly identified monoclonal antibodies exhibit the following: 1) a higher affinity for the CA 125 glycoprotein, thereby providing the basis for an assay system which could detect relatively low levels of serum CA 125; 2) are capable of recognizing the cell surface of tumor cells, thereby providing a means of radioisotope imaging or delivering therapeutic agents for diagnostic and treatment purposes; and 3) are able to recognize individual domains of the CA 125 molecule for mapping of the biologically active sites of the CA 125 molecule, thereby providing insight into the normal functions of the CA 125 antigen.

One of the newly identified monoclonal antibodies, M2, competes with OC 125 for binding to the CA 125 antigen. It recognizes large molecular weight subunits of CA 125 similar to OC 125 and similar to the purified subunits described by Davis et al., Cancer Res, 46:6143–6148 (1986). M11, a second monoclonal antibody, does not compete for the OC 125 binding site, but does immunoprecipitate multiple CA 125 subunits similar to M2. OC 125 recognizes a major subunit of those precipitated by M2 and M11. Even though these two antibodies recognize similar CA 125 subunits, immunolocalization of the antigen using the amnion as a test system indicates a significant difference in cellular distribution of determinants recognized by these two antibodies. In fact, M2 is almost entirely localized within the amniotic epithelium and is relatively evenly distributed throughout the cytoplasm. In contrast, M11 is almost exclusively localized to the extracellular glycocalyx matrix and appears to have a much lower recognition of the intracellular antigen than M2. Antibody recognition of antigen localized to the extracellular matrix is of interest because drug delivery or imaging systems are best directed with antibodies recognizing the cell surface.

On the other hand, cytoplasmic recognition of the antigen is most important for antibodies which might be used to screen cDNA libraries, where antibodies which recognize protein espitopes with no post translational modifications are desired. Both the M1 antibody which recognizes a unique 68 kd subunit of the CA 125 molecule and the M2 antibody which recognizes high molecular weight subunits of the CA 125 molecule are localized in the cytoplasm. The availability of these new antibodies will indeed improve our ability to; (a) further define the CA 125 molecule and its constituent domains; (b) screen and potentially identify the CA 125 gene(s); (c) facilitate direct immunopurification of the CA 125 antigen; (d) further enhance our ability to detect and specify tumor CA 125 antigen in patient sera; and (e) direct chemotoxic agents or imaging isotopes to the surface of peritoneal tumor cells.

It should be understood that various changes and modifications to the presently preferred embodiments described herein will be apparent to those skilled in the art. Such changes and modifications can be made without departing from the spirit and scope of the present invention, and without diminishing its attendant advantages. It is therefore intended that such changes and modifications be covered by the appended claims.

I claim:

1. A monoclonal antibody wherein said antibody is identified as M 11.

2. The monoclonal antibody of claim 1, wherein M11 has a binding affinity for a subunit of CA 125 epitope having a molecular weight of greater than approximately 200 k daltons.

3. The monoclonal antibody of claim 1, wherein M11 is located predominantly in the extracellular matrix of CA 125 producing cells wherein M11 is bound to a CA epitope.

4. A hybridoma cell line capable of producing antibody M 11.

5. A monoclonal antibody for use in delivering therapeutic agents to tumor cells, wherein the monoclonal antibody is identified as M11 according to claim 3.

6. A monoclonal antibody for use in directing imaging agents to tumor cells, wherein the monoclonal antibody is identified as M11 according to claim 1.

7. A monoclonal antibody for use in detecting CA 125 in paraffin fixed secretions of human tissues, wherein the monoclonal antibody is identified as M11 according to claim 1.

* * * * *